United States Patent [19]
Dusek

[11] Patent Number: 4,863,464
[45] Date of Patent: Sep. 5, 1989

[54] INTRAOCULAR LENS

[75] Inventor: Vaclav Dusek, Renton, Wash.

[73] Assignee: The Cooper Companies, Inc., Bellevue, Wash.

[21] Appl. No.: 148,598

[22] Filed: Jan. 26, 1988

[51] Int. Cl.$^4$ ............................................. A61F 2/16
[52] U.S. Cl. ........................................................ 623/6
[58] Field of Search ............................................ 623/6

[56] References Cited

U.S. PATENT DOCUMENTS

| | | | |
|---|---|---|---|
| 4,418,431 | 12/1983 | Feaster | 623/6 |
| 4,441,217 | 4/1984 | Cozean | 623/6 |
| 4,494,254 | 1/1985 | Lopez | 623/6 |
| 4,502,163 | 3/1985 | Graham | 623/6 |
| 4,542,540 | 9/1985 | White | 623/6 |
| 4,575,878 | 3/1986 | Dubroff | 623/6 |
| 4,588,405 | 5/1986 | Knolle, Jr. | 623/6 |
| 4,601,721 | 7/1986 | Kamerling | 623/6 |
| 4,681,586 | 7/1987 | Woods | 623/6 |
| 4,737,322 | 4/1988 | Bruns et al. | 623/6 X |

FOREIGN PATENT DOCUMENTS 8500527  1/1986  Netherlands ............................ 623/6

OTHER PUBLICATIONS

"The Intraocular Implant Lens Development and Results with Special Reference to the Binkhorst Lens", (Book) by M. E. Nordlohne, Second Edition, The Williams & Wilkins Company–Baltimore, 1975, pp. 14–20, the Barraquer Lens Shown in FIG. 4 on p. 16, Relied Upon.
"Clayman 7mm Ovoid One-Piece", Lens Model No. 5770 and 5772 UV, Advertisment Brochure by Precision Cosmet (1 p.), 1985.

Primary Examiner—Ronald L. Frinks
Attorney, Agent, or Firm—Pravel, Gambrell, Hewitt, Kimball & Krieger

[57] ABSTRACT

An intraocular lens having one or more flexible haptic support loops connected to an optic. Each haptic support loop includes a first segment connected to the optic and extending therefrom at an acute angle relative to the optic periphery, a second segment extending from the first segment in an arc having at least one radius of curvature smaller than the radius of the optic and at least one radius of curvature on the side of the haptic opposite the acute angle formed by the first segment, and a third segment extending from the second segment in an arc having one or more radii of curvature greater than the radius of the optic which terminates in a free end spaced outwardly from the optic periphery. The first segment extends from the optic substantially parallel to a horizontal reference line (HR) on the optic and the second segment extends beyond a reference line that is parallel to a vertical reference line (VR) on the optic and tangent to the outer peripheral edge of the optic with the free end of the third segment located in a quadrant formed by the horizontal and vertical reference lines that is adjacent to the quadrant in which the second segment is located. This support loop shape results in a highly flexible haptic with characteristics similar to those of the traditional open-loop haptic through a first small amount of compression, but then results in a greater stiffness after the support loop is compressed further.

20 Claims, 5 Drawing Sheets

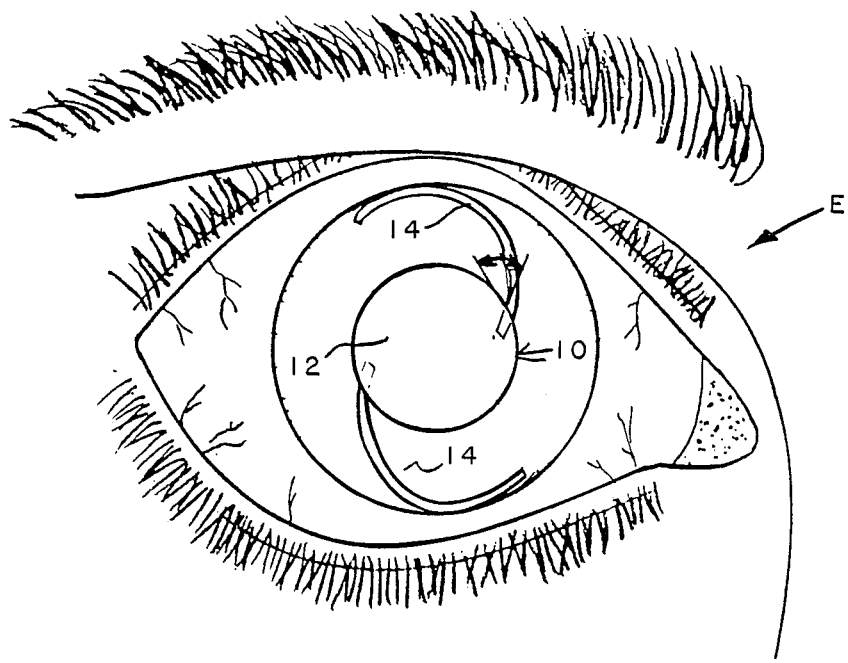
FIG. 1A
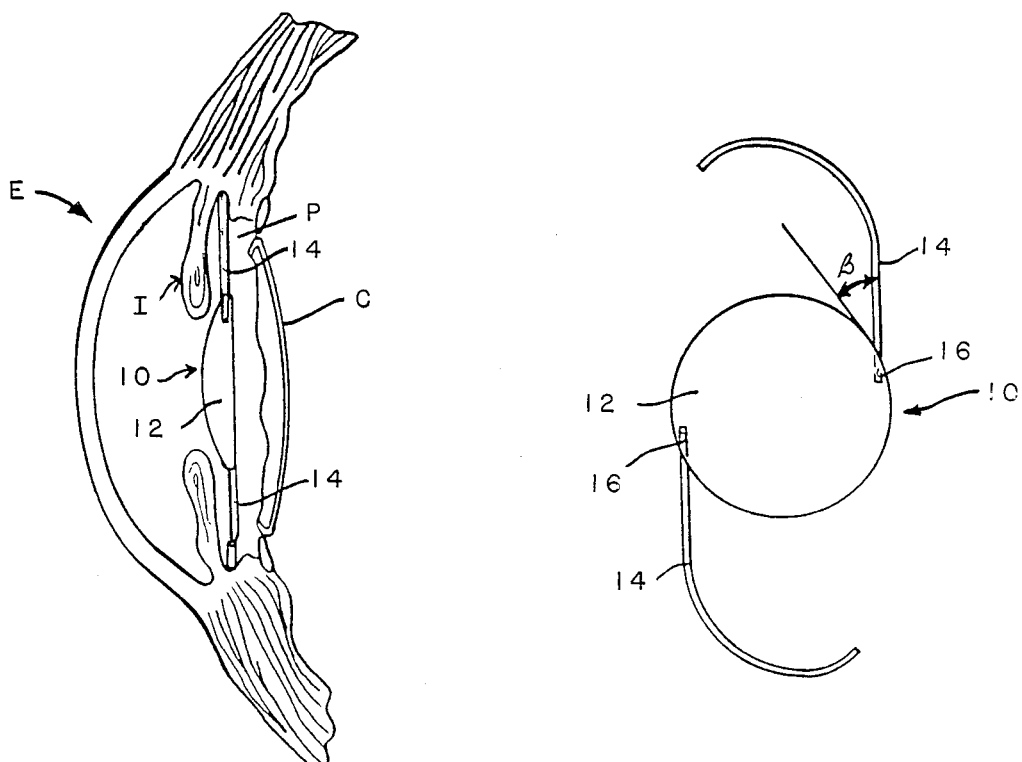
FIG. 1B
FIG. 2A

INTRAOCULAR LENS

BACKGROUND OF THE INVENTION

1. Technical Field of the Invention

This invention relates to intraocular lenses (IOLs), which are to be implanted in the eye to replace a natural lens that has been removed because of cataract or other reasons. More particularly, this invention relates to an IOL with an uniquely-shaped support loop or haptic designed to be implanted in the posterior chamber of the eye.

2. Background of the Invention

There are many IOLs of varied shapes on the market, which are used to replace the natural lens of the eye after extra-capsular surgery where the natural lens of the eye is removed. Such lenses include an optical portion and one or more support loops or haptics, which retain the IOL optic in the eye in its desired position either in front of the iris in the anterior chamber or to the rear of the iris in the posterior chamber.

The support loops retain the IOL in a relatively fixed position so that light can be focused on the retina. It is advantageous for the support loops to be flexible in order to accommodate changes in shape of the eyeball without causing damage to any of the interior portions of the eye in contact with the support loops.

IOLs can be formed of a single-piece of material such as polymethylmethacrylate (PMMA) where the support loops are formed integral with the optic portion through casting, machining or lathe cutting methods. Other types of IOLs, called multi-piece lenses, can also be formed where support loops made of a material such as polypropylene or PMMA (VS-100) are attached to an optic portion by heat welding or through laser welding, ultrasonic welding or other methods.

Haptics can be formed of a stiff material, but they are more often flexible in order to facilitate positioning of the lens in the proper location while accommodating for changing shapes of the eyeball. The haptic design, including its flexibility, is considered to be important in achieving maximum patient comfort and lack of post-operative complications, ease of implantation and effectiveness of maintaining the lens in its proper position.

Haptic shape is also an important consideration in connection with surgical procedures and the size of an incision in the eye through which an IOL can be inserted. Smaller incisions are desirable in order to reduce astigmatic effects caused by distortion of the eyeball after surgery is completed. For IOLs with optics formed of a relatively stiff material, it is desirable for haptics to be designed so that they can be manipulated to overlap the optic portion during insertion so the incision can be formed only slightly larger than the optic diameter.

Typically, haptics are constructed so as to generate a reactive force as a result of any movement of the IOL in the eye. This reactive force has an axial component that assists to some extent in maintaining an IOL in its proper axial position relative to the plane of the optic. Also, the reactive force has a radial component directed toward the center of the optic which tends to maintain the lens in its proper radial position in order to insure proper image projection on the retina. This radial component must be great enough to hold the lens in position and small enough to allow the haptics to flex without causing irritation to the eye structure. Thus, haptics must be sufficiently flexible to generate these reactive forces in the proper amount regardless of the changes in the shape of the eye.

Currently known haptic designs do not achieve optimum reactive force in the radial or axial directions. Because of the orientation of the haptics relative to an optic and because of the shape and the length of the support loops themselves, contact points between the support loops and surrounding eye structure are to some degree limited to a narrow sector that extends radially outward from the center of the lens with respect to the attachment point of the support loop on the periphery of the optic. As a result, lenses that are too flexible can become de-centered where the radial reactive force is not sufficient to maintain the lens in its proper position as the eyeball distorts.

Another problem in connection with the fabrication of IOLs is that some physicians prefer lenses where the support loops are formed coplanar with the optic, while others believe that IOLs with support loops designed to project at an angle relative to the plane of the optic are desirable. For most multipiece IOLs of this nature, the manufacturing process must be altered in order to fabricate a lens with angled support loops by drilling the holes in the optic at this angle, into which the support loops are inserted. This complicates the manufacturing process since a different tooling and technique for drilling holes for these angled haptics is required than for the ones coplanor with the optic. Also, this complicates an inventory since plano and angled optics must be built and stored separately.

An example of an IOL that is considered to provide beneficial characteristics for implantation in the posterior chamber has support loops that are open ended and project radially outwardly from opposite sides of an optic. Such lenses are commonly referred to as J-loop or C-loop lenses, or the like, and are characterized by a curved-loop configuration that ends at a point spaced from the periphery of the optic portion. A number of variations of this lens style have curved loops with varying degrees of contact with the interior of the eye.

The loops can be manipulated to overlap the optic during insertion to minimize the length of an incision. However, because of the long shape of the loops they are believed to be overly flexible and tend to de-center in the eye after implantation. Further, in order to form lenses with such loops where the loops are oriented at an angle relative to the plane of the optic, holes must be drilled in the optic at that angle instead of in the planar direction.

SUMMARY OF THE INVENTION

The problems and difficulties described above in connection with the open-ended C-loop style posterior chamber IOLs other posterior chamber IOLs with variations on open-ended loop configurations known as the C, modified-C, J, modified-J and other variations, are solved by an IOL with a loop design of the present invention. While the invention is illustrated with a smooth loop that has a broad sweeping portion which engages the eye along a substantial portion of its length, other designs could be used in conjunction with the invention which have varying degrees of contact with the eye.

The IOL of the present invention has one or more support loops that are connected to an optic formed of rigid or foldable material, either as a single-piece lens formed of a single piece of plastic or as a multi-piece IOL where support loops are attached to a separate optic portion.

Each support loop includes a segment connected to the optic, which forms an acute angle relative to the periphery of the optic. Another segment of the support loop extends from the first segment and has one or more radii of curvature smaller than the radius of curvature of the optic. The center or centers of curvature of the second segment are on the side of the haptic opposite the acute angle formed between the first segment and the periphery of the optic. This location of the center or centers of curvature of the second segment causes the support loop to reverse its angular direction and double back past its attachment point to the periphery of the optic.

The support loop also includes a third segment having one or more radii of curvature larger than the radius of the curvature of the optic. This results in the support loop having a broad sweeping shape with a portion that comes in contact with the interior of the eye, which is similar to the contact portion for a traditionally-shaped C-loop or modified C-loop IOL. This support loop shape results in a highly flexible lens with characteristics similar to those of the traditional open-loop lens through a first small amount of compression, but then results in greater stiffness after the support loops are compressed further. This tends to resist de-centering of the optic to a greater degree than typical C-loop lenses and other haptic designs.

Further, when the subject invention is used in conjunction with a multi-piece lens, the support loops can be connected to the optic portion in holes drilled coplanar with the optic regardless of the axial orientation of the support loops relative to the plane of the optic. This results in a single manufacturing process for drilling holes in the optic portions and simpler inventory system for IOLs with both plano and angled support loops.

BRIEF DESCRIPTION OF THE DRAWINGS

A better understanding of the invention can be obtained when the detailed description of exemplary embodiments set forth below is considered in conjunction with the appended drawings, in which:

FIG. 1A is a front schematic view of a human eye with a known open-ended loop IOL known as a C-loop, implanted in place;

FIG. 1B is a side schematic view of the eye and lens of FIG. 1A;

FIGS. 2A and 2B are front plan views of examples of other IOLs with open-ended loops, known as a modified C-loop IOL and a modified J-loop IOL, respectively;

FIG. 14A and FIG. 14B are force-compression charts showing a reactive haptic force in gram-force versus haptic compression in millimeters.

DETAILED DESCRIPTION OF EXEMPLARY EMBODIMENTS

Figure 2B:
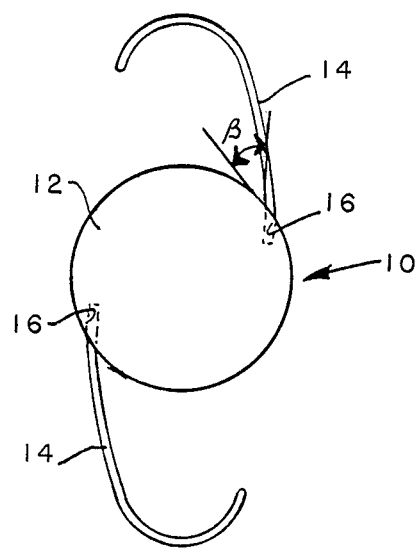

Referring to FIGS. 1A and 1B, a typical known IOL with open-ended loops, generally designated by reference numeral 10, is shown implanted in a human eye E, in a space known as a posterior chamber P that is located between an iris I and a portion of a capsular bag C that is left after the natural lens (not shown) has been removed. The IOL 10 includes an optic portion 12 and support loops 14. As shown, the support loops 14 are generally open-ended with portions that are designed to contact the interior portion of the eye E known as the ciliary sulcus. The IOL of FIGS. 1A and 1B is known as a C-loop IOL, while other known open-ended loop IOLs as shown in FIGS. 2A and 2B, using the same reference numerals used in FIGS. 1A, 1B are known as modified C-loop and modified J-loop IOLs. These and other similar styles of open-ended loop IOLs are examples of IOLs over which the present invention is an improvement.

The IOLs 10 are formed as multi-piece lenses, which means that the support loops 14 are formed of pieces of material separate from the material used to form the optic 12 and are inserted into holes 16 formed in the optic and then heat welded by known techniques so that the support loops 14 are anchored in the holes 16. Typically, the optic portion is formed of PMMA while the support loops are formed of either polypropylene or extruded PMMA. However, support loops configured in accordance with the invention could be used with optic portions formed of what is known as the "soft" materials such as hydrogels, acrylics or other soft materials known in the art.

Figure 3A:
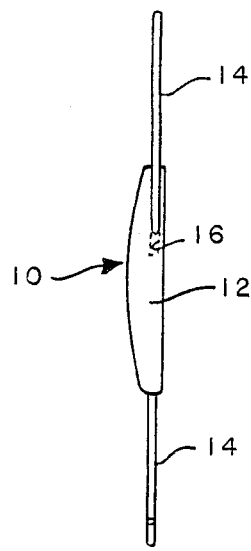
FIGS. 3A and 3B are side plan views of examples of IOLs of the type shown in FIGS. 1A, 2A and 2B, showing the loops respectively formed coplanar with and at an angle relative to the plane of the optic.
Figure 3B:
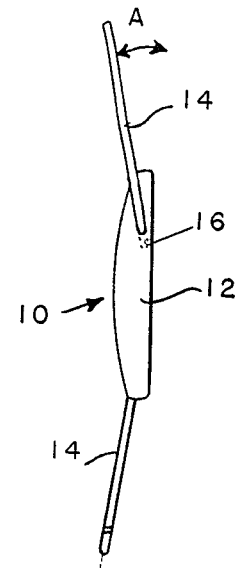

As shown in FIG. 3A, when the loops 14 are formed in the same plane as the optic portion 12 the holes 16 are drilled in the periphery of the optic parallel to the plane of the optic 12. However, as shown in FIG. 3B, when the loops 14 are oriented at an angle A, typically 10°, relative to the plane of the optic 12, the hole 16 must be drilled at an angle relative to the plane of the optic 12. This results in having to change the production process for fabricating the optics 12 when angulated loops as shown are to be used.

An alternative to drilling the holes 16 at an angle A relative to the plane of the optic 12 is to connect the loops 14 coplanar as shown in FIG. 3A and then place the IOL 10 in a die (not shown) for bending the loops 14 to the desired angle. This latter technique also requires an extra production step.

Further, as shown in FIGS. 1A, 1B, 2A and 2B, typical lenses of the type shown with open-ended loops are formed such that the portion of the loop connected directly to the optic 12 curves toward an acute angle B formed between the portion of the support loop 14 that is inserted in the hole 16 relative to the periphery of the lens at that point of curvature (FIG. 1A) or follows the direction of a segment inserted in the hole 16 for a short distance and then curves toward the acute angle B (FIG. 1B). As mentioned above, it is believed that while under compression in the eye for short distances the loops shaped as shown in FIGS. 1A, 1B, 2A and 2B provide the type of flexibility that is desirable for maintaining a reasonable contact area within the eye without being overly stiff. When the eyeball distorts beyond a certain minimum level, however, the loops 14 are believed to be too flexible to maintain the position of the lens 10 within the eye so that it remains centered.

Figure 4:
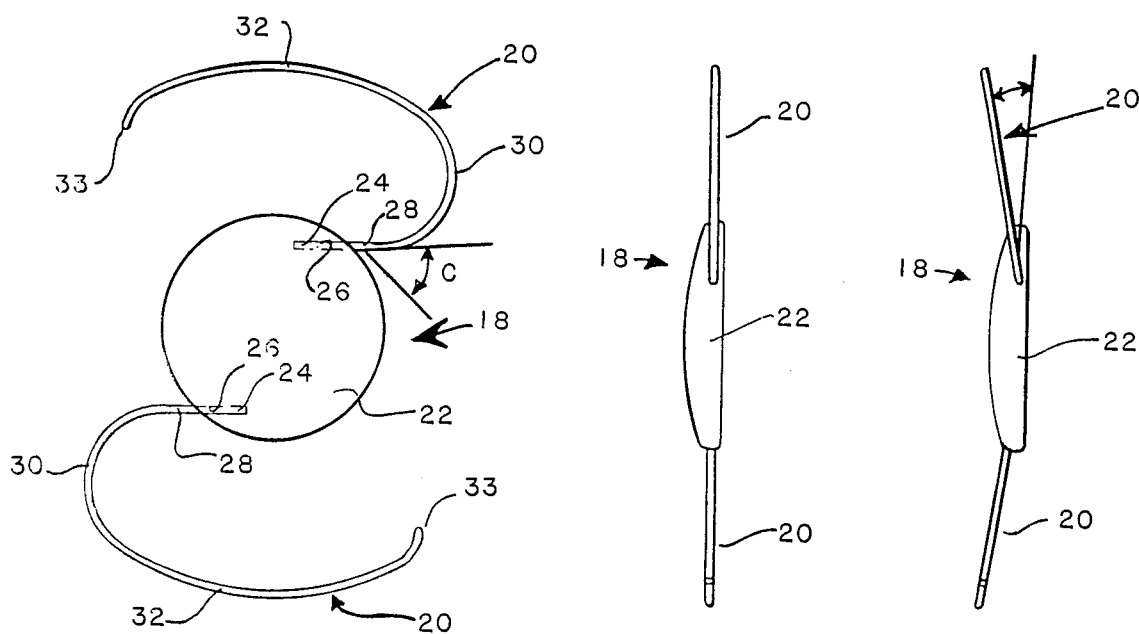
FIG. 4 is a front plan view of one embodiment of the invention.

FIG. 4 shows an IOL 18 with open-ended loops 20 formed in accordance with the invention, which are attached to an optic portion 22. The lens shown in FIG. 4 is a multi-piece lens where the support loops 20 are formed of pieces of material separate from the material used to form the optic 22 and then attached or connected to the optic 22 through known methods. In accordance with the invention, the support loops 20 are connected to the optic 22 by insertion of a segment 24 into a hole 26 drilled in the periphery of the optic 22. The segment 24 can be anchored in place through the use of what is called a heat staking process where a heated probe is inserted through a portion of the optic and into the segment 24 to deform the segment and provide a mechanical interlock between the segment 24 and the portion of the optic 22 surrounding the opening 26.

The support loops 20 include a segment generally designated by reference numeral 28, which emerges from the hole 26 and extends from the optic portion 22 in such a way as to form an acute angle C between a tangent of one side of the segment 28 at the point where the segment 28 emerges from the hole 26 and the tangent to the periphery of the optic portion 22 at the same point. The support loop 20 further includes a segment 30 that extends from the segment 28 in an arc having one or more radii of curvature smaller than the radius of the optic portion 22 and a center or centers of curvature on the side of the haptic portion opposite the acute angle C so that the support loop reverses its angular direction and doubles back past where it is attached to the optic 22.

The support loop also includes a segment generally designated by reference numeral 32, which extends from the segment 30 in an arch having one or more radii of curvature greater than the radius of the optic portion 22. The segment 32 can be formed as a smooth curve as shown or equipped with notches (not shown) for easier manipulation during implantation. The segment 32 terminates in a free end portion 33 that can be rounded or otherwise shaped for easier manipulation.

In this way, a support loop 20 is formed that has a contact portion greater than the IOLs shown in FIGS. 1A, 1B, 2A and 2B for contact within the eye. As discussed in greater detail below, the IOL 18 has flexibility characteristics similar to the IOL shown in FIGS. 1A, 1B, 2A and 2B during initial stages of compression, but is stiffer during any further compression. The preferred angle formed between the second segment 28 and the periphery of the optic portion 22 is approximately 40°, although it is believed that any acute angle will work with at least some degree of improvement over the lenses shown in FIGS. 1A, 1B, 2A and 2B.

The improved compression characteristics of the IOL that is the subject of the invention are illustrated in the charts set forth below where the results of compression tests conducted on various IOLs are shown.

Figure 11:
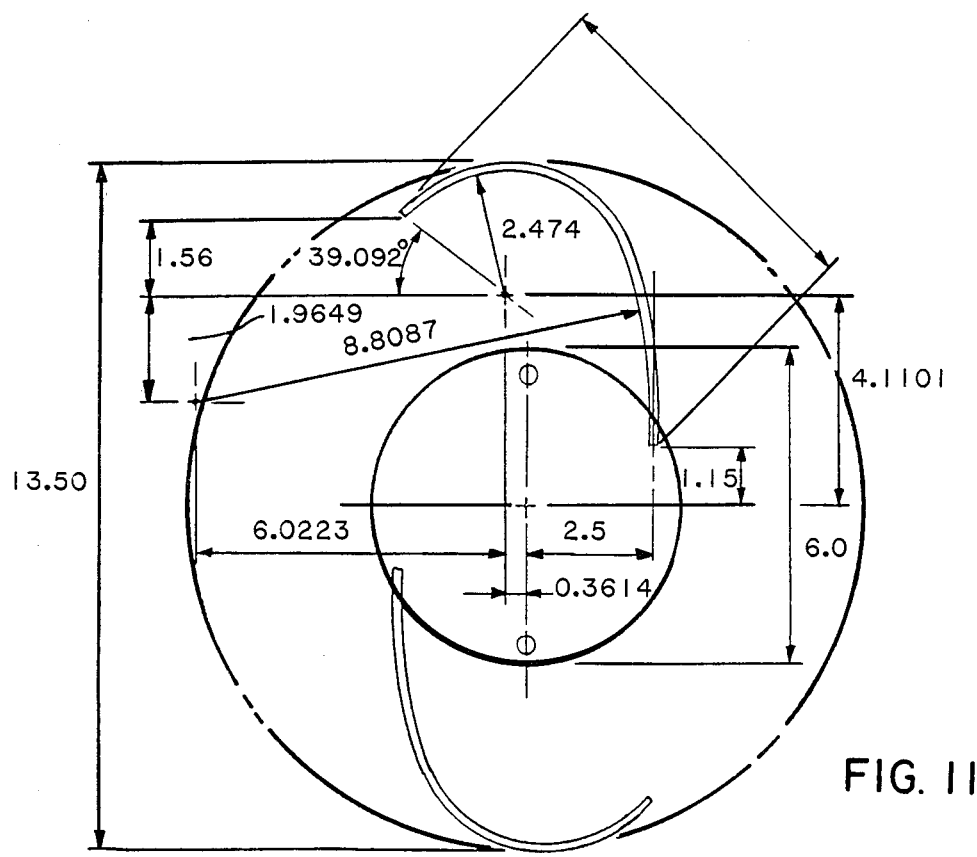
FIG. 11 is a front view of a lens similar to the one in FIG. 2A, showing dimensions and centers of curvatures.

Dimensions of one type of an open-ended loop lens in the prior art are shown in FIG. 11 where the overall diameter including haptics is 13.50 mm, the diameter of the optic portion of 6 mm and the radius of the arc of the haptic is 2.474 mm, with other dimensions and locations of centers of curvature shown in FIG. 11. The loop material was extruded PMMA of a type commonly used in IOLs of the style shown.

Figure 12:
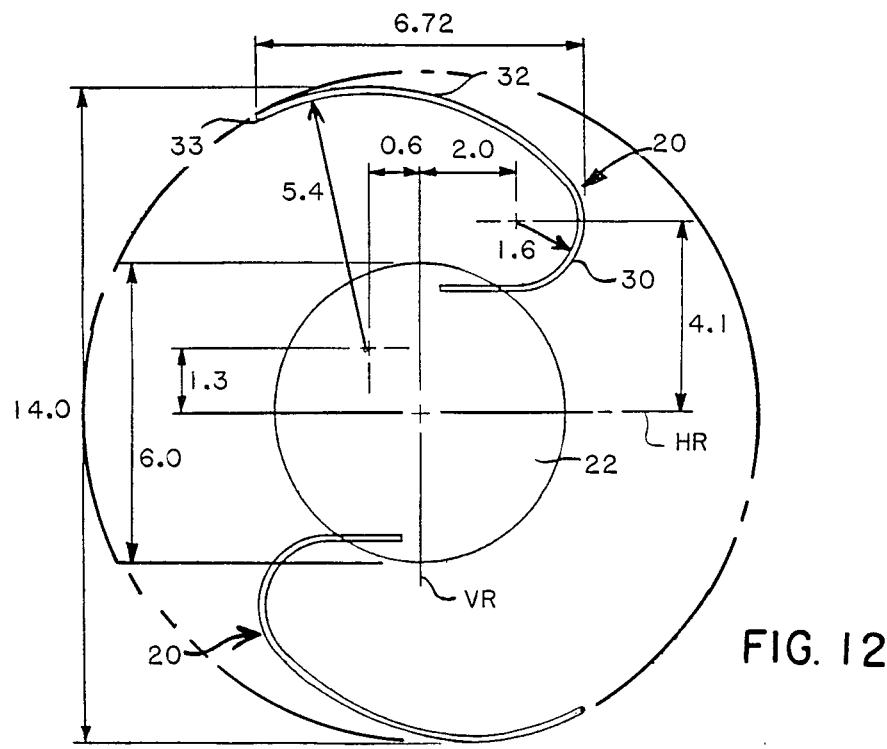
FIG. 12 is a front plan view of a lens similar to the one in FIG. 4, showing dimensions and centers of curvature.

FIG. 12 shows the pertinent dimensions of a lens made in accordance with the present invention that was also tested. The optic portion 22 has a diameter of 6.00 mm while the overall diameter of the IOL including two support loops in a free state is about 14 mm. The support loops were formed of extruded PMMA, similar to those in the IOL of FIG. 11. Segment 30 of support loop 20 has a radius of curvature of 1.6 mm and a center of curvature defined by a horizontal coordinate of 2.0 mm along horizontal reference line HR and a vertical coordinate of 4.1 mm along vertical reference line VR. Segment 32 of support loop 20 has a radius of curvature of 5.4 mm and a center of curvature defined by a horizontal coordinate of 0.6 mm along horizontal reference line HR and a vertical coordinate of 1.3 mm along vertical reference line VR. As used, the terms horizontal and vertical refer only to the angular orientations of the reference lines in FIG. 12, the only purpose of which is location of the centers of curvature in this description. Finally, the horizontal dimension from the free end 33 of support loop 20 to the outside of the arc of segment 30 is 6.72 mm.

As shown in the compression FIG. 14A, the loop design shown in FIG. 12 results in the generation of a greater reactive haptic force after compression of about 2 mm, than the haptic force found in the IOL of FIG. 11.

The line "— ◊ —" represents the compression tests on the IOL shown in FIG. 11 with a support loop angle A (FIG. 3B) of 10°, while the lines "—□—" and "—+—" represent compression tests on IOLs of FIG. 12 with support loop angles of 0° and 10°, respectively.

The line "— ◊ —" of FIG. 14A shows a reactive haptic force in units of gram-force versus haptic compression in millimeters in connection with tests performed on the IOL in FIG. 11. One gram-force is equivalent to approximately 981 dynes. As compression of the haptic increases from 1.5 to 3.0 millimeters it can be seen that the reactive haptic force increases from about 0.175 to about 0.36 gram-force.

The line "—+—" shows the same force versus compression relationship in support loops formed in accordance with the present invention as shown in FIG. 12, with the loops oriented at an angle A of 10° (See FIG. 3B). It can be seen that an increase in haptic compression from about 1.5 to 3.0 millimeters results in an increase in reactive haptic force from about 0.10 to about 0.60. In the style of IOLs shown in FIG. 11 an additional 1.5 millimeter haptic compression results in an additional reactive haptic force of only 0.185 gram-force. On the other hand, in the lens made in accordance with the invention as shown in FIG. 12, an increased haptic compression of about 1.5 millimeter results in an increase in reactive haptic force of about 0.50 gram-force.

This increase in reactive haptic force over compression of 1.5–3.0 mm means that the resistance of the support loop against radial movement of the optic over that distance is between 2½ and 3 times as great in the lens of the invention as compared to the prior art lenses. This increase in resistance is achieved because of the relatively stiff spring-like action of the loops 20 resulting from doubling the haptic back over its attachment point as shown in FIG. 12.

The line "_▫_" illustrates that the increase in reactive haptic force resulting from a similar compression of the lens of FIG. 12, where the support loops are coplanar with the optic, is from about 0.05 gram-force to about 1.0 gram-force, an increase of 0.95 gram-force.

Additional evidence of the greater resistance of the IOL of present invention after a predetermined initial compression, compared with known IOLs is shown in FIG. 14B below, where compression curves for an IOL of the type shown in FIG. 13, which is similar to the one shown in FIG. 2B, with a loop angle A of 10° are shown. In FIG. 14B the line "_▫_" represents tests on such an IOL with extruded PMMA loops, while the line "_△_" is for such an IOL with polypropylene loops.

Figure 13:
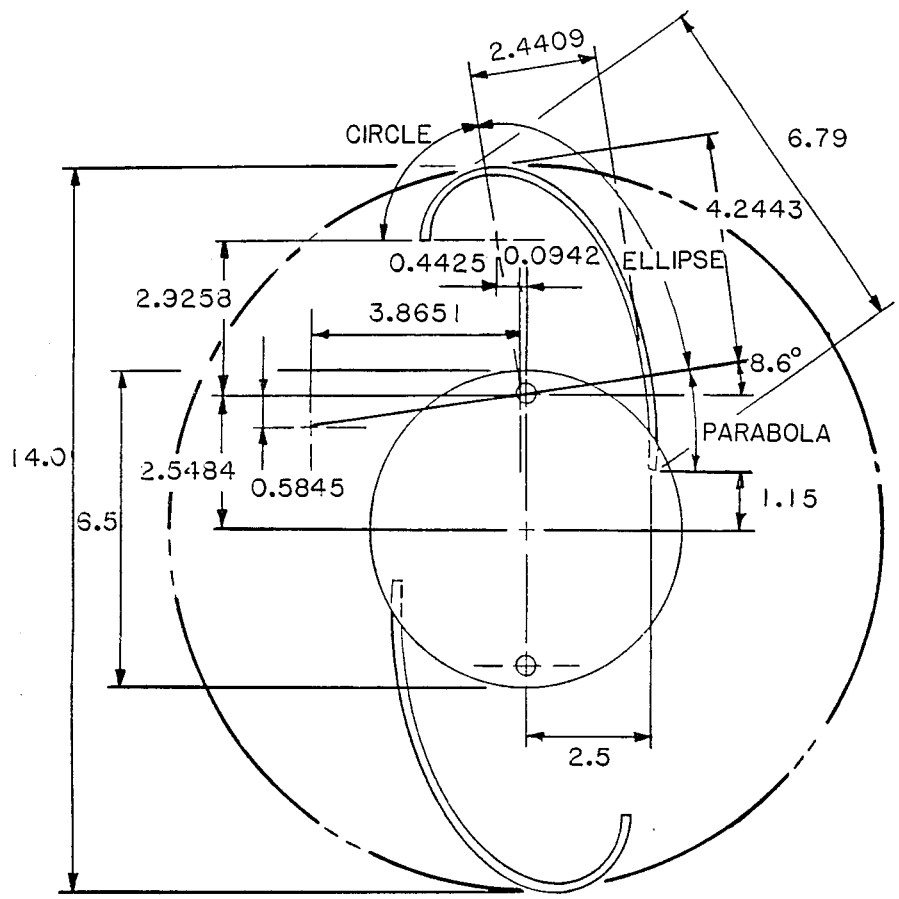
FIG. 13 is a front plan view of a lens similar to the one in FIG. 2B, showing dimensions and centers of curvature.

As shown, the IOL 10 of FIG. 13 has an outer loop diameter of 14.0 mm and an optic diameter of 6 mm. The segment lengths and centers of curvature for the loops 14 are also shown.

As shown in FIG. 14B the IOL 10 in FIG. 13 with PMMA haptics (line "_▫_") has a compression profile similar to the IOL of FIG. 11 as shown in FIG. 14A (line "_◊_").

Further, the polypropylene loops 14 of the IOL 10 of FIG. 13 are overall more flexible than the loops of an identical IOL formed of PMMA, as shown by the shallower slope of the curve "_△_". Thus, it can be concluded that IOL loops formed in accordance with the present invention as shown in FIG. 12 provide a greater resistance to compression after at least about 2 mm of compression, which it is believed, will provide greater resistance to decentering, and that the same is true for polypropylene as well as PMMA support loops.

Figure 5:
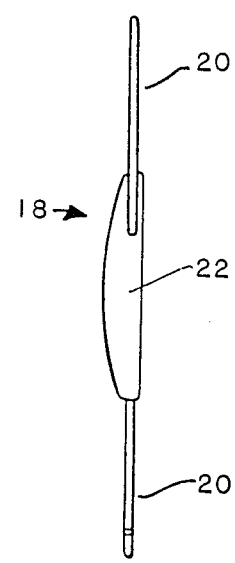
FIG. 5 is a side plan view of the IOL shown in FIG. 4 where the support loops are formed coplanar with the optic.
Figure 6:
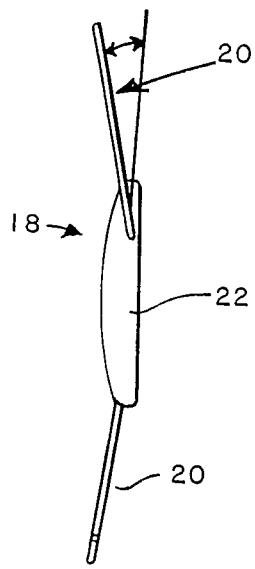
FIG. 6 is a side plan view of the IOL of FIG. 4 where the support loops are formed at an angle relative to the plane of the optic.

A further advantage of the lens shown in FIG. 12 is illustrated in the side views of FIGS. 5 and 6. FIG. 5 shows the IOL 18 formed with the support loops 20 oriented in the same plane of the optic portion 22. As shown, the hole 26 in which the segment 24 of each support loops 20 is inserted is drilled in the periphery of the optic portion 22 parallel to the plane of the optic portion 22.

As shown in FIG. 6, when the support loops 20 are formed at an angle A relative to the plane of the optic portion 22, the hole 26 is still drilled in the periphery of the optic portion parallel to its plane so that a separate fabrication process for forming optics for use with angulated loops does not have to be made. In other words, the same orientation of the holes 26 can be used for planar loops as well as angulated ones. The angle A is achieved simply by rotating the loops 20 in their respective holes 26.

Figure 7:
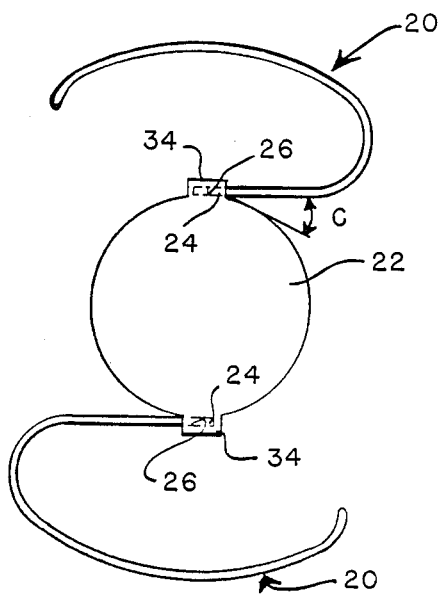
FIG. 7 is a front plan view of a second embodiment of the invention as used in conjunction with a multi-piece lens.

The IOL shown in FIG. 4 has a pair of support loops that are located on opposite sides of the optic portion 22 and are identical in shape to each other. The support loops 20 can be connected at any portion along the periphery of the optic portion 22 as long as an acute angle C is formed as described. Instead of having the support loop 20 connected directly to the optic portion 22, radially projecting tabs 34 as shown in FIG. 7 can be formed on the periphery of the optical portion 22. Openings 26 similar to those shown in FIG. 4 can be formed in the tabs 34 and the segments 24 of the support loops 20 are inserted in the holes 26. Even though the support loops 20 are connected to the optic portion 22 outside of the area within the circumference of the optical portion 22, the same type of support loops as described in conjunction with FIG. 4 can be used which include a segment 28 that extends from the holes 26 to form an acute angle C between the tangent of one side of that segment and the tangent of the periphery of the optic 22.

Figure 8:
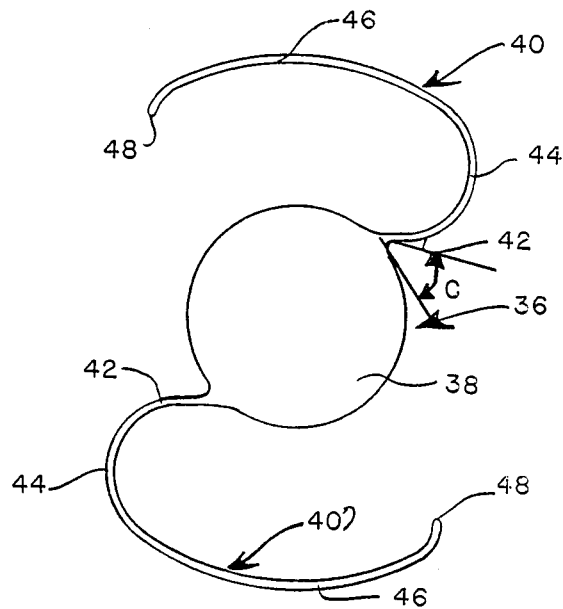
FIG. 8 is a front plan view of a third embodiment of the invention as used in conjunction with a single-piece lens.

The invention can also be used in conjunction with single-piece lenses such as the one designated by reference numeral 36 in FIG. 8. This type of lens includes an optic portion 38 and support loops 40 that are formed of a single-piece of material. As shown in FIG. 8, a segment 42 of the support loops 40 adjacent to the periphery of the optic 36 is oriented to form an acute angle C relative to the periphery of the optic 38. Similar to the support loops shown in conjunction with the lenses of FIGS. 4 and 7, the support loops 40 as shown in FIG. 8 include a segment 44 that extends from the segment 42 that is connected to the optic 38, in an arch having one or more radii of curvature smaller than the radius of the optic portion 38, with the center or centers of curvature being on the side of the support loop opposite the acute angle C. The support loops 40 also include another segment 46 that extends from the segment 44 in a arch having one or more radii of curvature greater than the radius of the optic portion and terminating in a free end 48.

Figure 9:
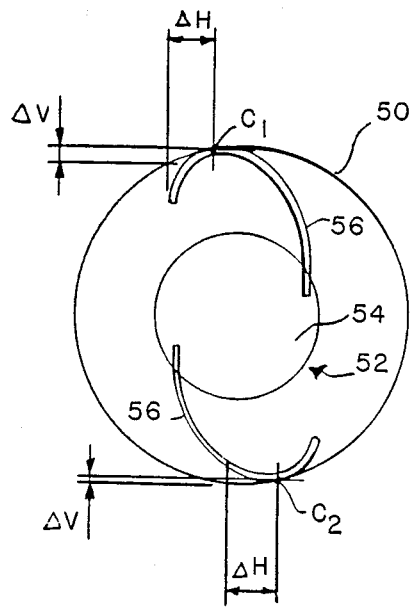
FIG. 9 is a front schematic view of a modified C-loop lens in an eye, showing displacement distance ΔH versus haptic compression ΔV.
Figure 10:
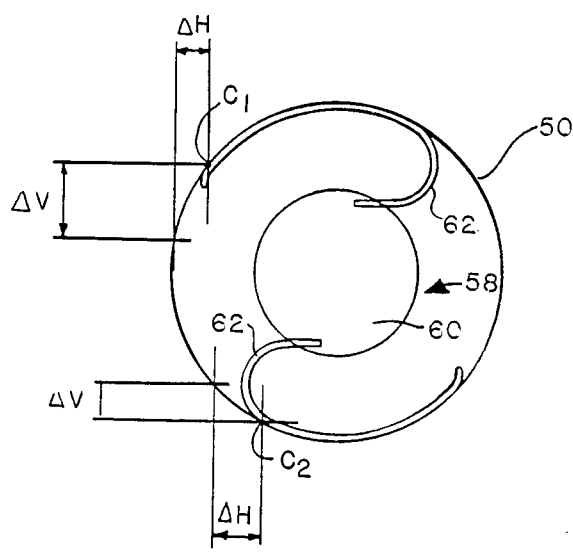
FIG. 10 is a front schematic view of a lens made in accordance with the invention, showing displacement distance ΔH versus haptic compression ΔV.

With IOLs of the types shown in FIGS. 4–8, support loops are shown with broad sweeping contact segments similar to the open-ended loop stype lenses shown in FIGS. 1A, 1B, 2A and 2B. However, the operation of the respective lenses in the eye differs significantly as shown in conjunction with the schematic drawings of FIGS. 9 and 10. As shown in FIGS. 9 and 10, an outer circle which represents the interior portion of the eye contacted by the support loops, is designated by reference numeral 50.

FIG. 9 shows an IOL 52 similar in style to the one of FIG. 1B within the eye 50, which has an optic portion 54 and support loops 56 shown in contact with the inner surface of the eye 50. Similarly, in FIG. 10, an IOL 58 formed in accordance with the invention is shown with an optic portion 60 and support loops 62 that are in contact with the inner surface of the eye 50.

Both of the lenses shown in FIGS. 9 and 10 have prime contact points between their respective support loops and the eye 50 that are designated by the letters C. It is believed that a horizontal movement of the support loops designated as $\Delta H$ takes place, which results in vertical displacement $\Delta V$ at points designated by reference letter C. In connection with the IOL 52 shown in FIG. 9, the $\Delta V$ is relatively small which creates a small haptic resistance against movement. For the same horizontal movement $\Delta H$ for the IOL 58 shown in FIG. 10, comparable vertical displacement $\Delta V$ is much larger, which creates a greater amount of resistance for the support loop 62 against movement.

Thus, by providing support loops in accordance with the invention, an IOL can be formed which has greater resistance to compression after an initial short distance than known IOLs. Thus, it is believed operates to resist decentering after the eye distorts to the point where the loops must compress beyond that initial distance. Further, in multi-piece IOLs, support loops can be attached coplanar with or at an angle relative to the flow of the optic without any addition for one compared with the other.

It should be understood that the embodiments of the invention described above are only illustrative and small variations in details and materials apparent to those skilled in the art can be made without departing from the spirit and scope of the invention as set forth in the appended claims.

I claim:
1. An intraocular lens, comprising:
   (a) an optically clear optic portion;
   (b) at least one flexible haptic portion connected to and projecting outward from the periphery of the optic portion;
   (c) the haptic portion including a first segment connected to the optic portion and extending from the optic portion an acute angle relative to the periphery of the optic portion;
   (d) the optic portion including horizontal (HR) and vertical (VR) reference lines, the first segment extending from the optic portion substantially parallel to the horizontal reference line;
   (e) the haptic portion including a second segment extending from the first segment in an arc having (i) at least one radius of curvature smaller than the radius of the optic portion and (ii) at least one radius of curvature on the side of the haptic portion opposite the angle formed by the first segment of the haptic portion and the periphery of the optic portion;
   (f) the second segment extending beyond a reference line that is parallel to the vertical reference line and which is tangent to the outer edge of the optic portion; and
   (g) the haptic portion including a third segment extending from the second segment in an arc having at least one radius of curvature greater than the radius of the optic portion, the third segment terminating in a free end in a quadrant formed by the horizontal and vertical reference lines adjacent to the quadrant in which the second segment is located.

2. The intraocular lens of claim 1, further comprising a second flexible haptic portion connected to the periphery of the optic portion diametrically opposite the first haptic portion and having first, second and third segments.

3. The intraocular lens of claim 2, wherein the optic and haptic portions are formed of a single piece of material.

4. The intraocular lens of claim 2, wherein the optic and haptic portions are formed of separate pieces of material that are connected together.

5. The lens of claim 1, wherein the first segment of the haptic portion is straight from the periphery of the optic portion to the second segment of the haptic portion.

6. The lens of claim 1, wherein the first segment of the haptic portion has at least one radius of curvature such that an acute angle is formed between (i) a line tangent to the first segment at its point of connection to the optic portion and (ii) a line tangent to the periphery of the optic portion at its point of connection to the first segment.

7. The lens of claim 1, wherein the optic portion includes at least one protuberance integral with the optic portion projecting generally radially from the periphery of the optic portion, the first segment of the haptic portion being connected to the protuberance.

8. The lens of claim 3, 4 or claim 7, further comprising a connecting segment of the haptic portion inserted in a hole in the optic portion such that the first segment of the haptic portion extends in a straight line for a short distance from the periphery of the optic portion.

9. The lens of claim 3, 4 or claim 7, further comprising a connecting segment of the haptic portion inserted in a hole in the optic portion such that the first segment of the haptic portion extends in an arc from the periphery of the optic portion.

10. The lens of claim 1, wherein the second segment of the haptic portion has a single radius of curvature for the entire length of the second segment.

11. The lens of claim 1, wherein the second segment of the haptic portion forms an arc having more than one radius of curvature.

12. The lens of claim 1, wherein the third segment of the haptic portion has a single radius of curvature for the entire length of the third segment.

13. The lens of claim 1, wherein the third segment of the haptic portion forms an arc having more than one radius of curvature.

14. The lens of claim 1, wherein the free end of the third segment of the haptic portion is located outwardly from the quadrant of the optic portion on the bisection line on which is located the point of connection between the haptic portion and the optic portion.

15. The lens of claim 1, wherein the haptic portion is coplanar with the periphery of the optic portion.

16. The lens of claim 1, wherein the haptic portion lies in a plane which interacts, at an acute angle, the plane in which the periphery of the optic portion lies.

17. The lens of claim 8, wherein the connecting segment of the haptic portion is straight and coplanar with the periphery of the optic portion and wherein the segments of the haptic portion which are external to the optic portion lie in a plane which intersects, at an acute angle, the plane in which the periphery of the optic portion lies.

18. The lens of claim 9, wherein the connecting segment of the haptic portion is in an arc and coplanar with the periphery of the optic portion and wherein the segments of the haptic portion which are external to the optic portion lie in a plane which intersects, at an acute angle, the plane in which the periphery of the optic portion lies.

19. The lens of claim 4, wherein the optic portion is formed of PMMA.

20. The lens of claim 4, wherein the optic portion is formed of a foldable material.

* * * * *